United States Patent
Talmer et al.

(10) Patent No.: US 8,211,386 B2
(45) Date of Patent: Jul. 3, 2012

(54) TAPERED CUVETTE AND METHOD OF COLLECTING MAGNETIC PARTICLES

(75) Inventors: Mark Talmer, Pepperell, MA (US); Kathleen Limerick, Pelham, NH (US); Gary Schroeder, Londonderry, NH (US)

(73) Assignee: Biokit, S.A., Barcelona (ES)

( * ) Notice: Subject to any disclaimer, the term of this patent is extended or adjusted under 35 U.S.C. 154(b) by 596 days.

(21) Appl. No.: 10/863,881

(22) Filed: Jun. 8, 2004

(65) Prior Publication Data

US 2005/0271550 A1    Dec. 8, 2005

(51) Int. Cl.
*B01L 9/00* (2006.01)
(52) U.S. Cl. .................................. 422/560; 422/562
(58) Field of Classification Search ............ 422/99–102, 422/560, 562; 436/524–526, 174, 175, 177, 436/180; 426/524–526, 174, 175, 177, 180
See application file for complete search history.

(56) References Cited

U.S. PATENT DOCUMENTS

| | | | |
|---|---|---|---|
| 3,627,432 A * | 12/1971 | Bergmann | 356/246 |
| 3,932,131 A | 1/1976 | Rolfo-Fontana | 23/230 R |
| 3,939,834 A | 2/1976 | McMahon | 128/272 |
| 3,952,599 A | 4/1976 | Ayres | 73/425.4 P |
| 3,977,794 A | 8/1976 | Liedholz | |
| 3,985,649 A | 10/1976 | Eddelman | 210/42 |
| 3,992,150 A | 11/1976 | Retzer | 23/230 |
| 4,022,577 A | 5/1977 | Brooker et al. | 23/230 B |
| 4,037,464 A | 7/1977 | Wenander | 73/61.4 |
| 4,046,515 A | 9/1977 | de Leeuw | 23/259 |
| 4,058,370 A | 11/1977 | Suovaniemi | 23/259 |
| 4,066,407 A | 1/1978 | Lupica | 23/230 B |
| 4,067,776 A | 1/1978 | Khan | 195/103.5 M |
| 4,141,687 A | 2/1979 | Forrest et al. | 23/230 R |
| 4,195,526 A | 4/1980 | Amos et al. | 73/425.6 |
| 4,229,104 A * | 10/1980 | Lahme et al. | 356/246 |
| 4,243,684 A | 1/1981 | Pruss et al. | 426/40 |
| 4,275,591 A | 6/1981 | Wand | 73/864.01 |
| 4,292,920 A | 10/1981 | Smith et al. | 118/425 |
| 4,361,032 A | 11/1982 | Lessnig et al. | 73/64.4 |
| 4,390,283 A * | 6/1983 | Meyer | 366/142 |
| 4,483,825 A | 11/1984 | Fatches | 422/100 |
| 4,526,046 A | 7/1985 | Oberli | 73/864.16 |
| 4,560,269 A * | 12/1985 | Baldszun et al. | 356/246 |
| 4,567,149 A | 1/1986 | Sell et al. | 436/513 |

(Continued)

FOREIGN PATENT DOCUMENTS

EP    0638809 A2    8/1994

(Continued)

OTHER PUBLICATIONS

Boehringer Mannheim Biochemicals, "Magnetic protAspheres," BMBiochemica, 1984, vol. 1 No. 3, pp. 1-2.

(Continued)

*Primary Examiner* — Jill Warden
*Assistant Examiner* — Dwayne K Handy
(74) *Attorney, Agent, or Firm* — Burns & Levinson LLP

(57) ABSTRACT

A vessel for use in clinical analysis including an open top, a closed bottom, and at least four tapered sides. A method for collecting magnetic particles in a fluid comprising the steps of providing a magnet and a vessel containing magnetic particles in a fluid, attracting the magnetic particles to the magnet, and moving the magnetic particles with the magnet out of the fluid.

6 Claims, 7 Drawing Sheets

U.S. PATENT DOCUMENTS

| | | | | |
|---|---|---|---|---|
| 4,592,338 A | 6/1986 | Blackmore | | 128/1 R |
| 4,622,847 A | 11/1986 | Paoletti et al. | | 73/61.4 |
| 4,677,067 A | 6/1987 | Schwartz et al. | | 435/177 |
| 4,678,752 A | 7/1987 | Thorne et al. | | |
| 4,692,609 A | 9/1987 | Pettersson | | 250/221 |
| 4,699,881 A | 10/1987 | Matschke | | 435/173 |
| 4,701,418 A | 10/1987 | Katopodis | | 436/64 |
| 4,721,680 A | 1/1988 | Jeffs et al. | | 436/180 |
| 4,748,128 A | 5/1988 | Katopodis | | 436/93 |
| 4,783,250 A | 11/1988 | Pons et al. | | 204/400 |
| 4,787,744 A | 11/1988 | Hissung | | |
| 4,790,176 A | 12/1988 | Marteau d'Autry | | 73/1 H |
| 4,793,973 A | 12/1988 | Ringrose | | 422/102 |
| 4,795,698 A | 1/1989 | Owen et al. | | 435/4 |
| 4,798,705 A | 1/1989 | Jakubowicz et al. | | 422/63 |
| 4,830,832 A | 5/1989 | Arpagaus et al. | | 422/65 |
| 4,873,875 A | 10/1989 | Cork | | 73/863.01 |
| 4,895,650 A | 1/1990 | Wang | | 210/222 |
| 4,904,396 A | 2/1990 | Benet | | 210/745 |
| 4,929,427 A | 5/1990 | Guala | | 422/100 |
| 4,931,257 A | 6/1990 | Quenin et al. | | 422/100 |
| 4,933,291 A | 6/1990 | Daiss et al. | | 436/45 |
| 4,962,044 A | 10/1990 | Knesel, Jr. et al. | | 436/177 |
| 4,970,892 A | 11/1990 | Enhorning | | 73/64.4 |
| 4,980,292 A | 12/1990 | Elbert et al. | | |
| 4,988,618 A | 1/1991 | Li et al. | | 435/6 |
| 5,009,847 A | 4/1991 | Solomons | | 422/61 |
| 5,010,930 A | 4/1991 | Columbus | | 141/1 |
| 5,013,529 A | 5/1991 | Itoh | | 422/100 |
| 5,026,526 A | 6/1991 | Quenin et al. | | 422/64 |
| 5,045,453 A | 9/1991 | Katopodis | | 435/18 |
| 5,068,089 A | 11/1991 | Ericsson et al. | | 422/61 |
| 5,084,041 A | 1/1992 | Oxley et al. | | 604/410 |
| 5,098,661 A * | 3/1992 | Froehlich et al. | | 422/102 |
| 5,104,621 A | 4/1992 | Pfost et al. | | 422/67 |
| 5,106,584 A | 4/1992 | Funakubo et al. | | 422/65 |
| 5,110,727 A | 5/1992 | Oberhardt | | 435/13 |
| 5,122,342 A | 6/1992 | McCulloch et al. | | 422/65 |
| 5,128,103 A | 7/1992 | Wang et al. | | 422/64 |
| 5,137,352 A | 8/1992 | Blitshteyn et al. | | 356/138 |
| 5,138,868 A | 8/1992 | Long | | 73/1 R |
| 5,141,871 A | 8/1992 | Kureshy et al. | | 436/47 |
| 5,147,529 A | 9/1992 | Lee et al. | | |
| 5,156,948 A | 10/1992 | Christensen et al. | | 435/5 |
| 5,158,895 A | 10/1992 | Ashihara et al. | | |
| 5,160,329 A | 11/1992 | Oxley | | 604/317 |
| 5,160,378 A | 11/1992 | Tuunanen et al. | | 134/25.1 |
| 5,167,922 A | 12/1992 | Long | | |
| 5,171,537 A | 12/1992 | Wainwright et al. | | 422/100 |
| 5,175,086 A | 12/1992 | Takekawa et al. | | |
| 5,183,638 A | 2/1993 | Wakatake | | 422/64 |
| 5,186,827 A | 2/1993 | Liberti et al. | | |
| 5,200,084 A | 4/1993 | Liberti et al. | | 210/695 |
| 5,200,151 A | 4/1993 | Long | | 422/100 |
| 5,232,665 A | 8/1993 | Burkovich et al. | | 422/65 |
| 5,250,262 A | 10/1993 | Heidt et al. | | 422/64 |
| 5,250,440 A | 10/1993 | Kelln et al. | | |
| 5,262,325 A | 11/1993 | Zimmermann et al. | | 435/269 |
| 5,268,147 A | 12/1993 | Zabetakis et al. | | 422/82 |
| 5,270,210 A | 12/1993 | Weyrauch et al. | | 436/43 |
| 5,271,896 A | 12/1993 | Jakubowicz et al. | | |
| 5,289,385 A | 2/1994 | Grandone | | 364/497 |
| 5,296,194 A | 3/1994 | Igarashi | | 422/82.05 |
| 5,334,538 A | 8/1994 | Parker et al. | | 436/525 |
| 5,340,749 A | 8/1994 | Fujiwara et al. | | 436/526 |
| 5,344,610 A | 9/1994 | Shaw | | 422/100 |
| 5,360,597 A | 11/1994 | Jakubowicz et al. | | |
| 5,399,497 A | 3/1995 | Kumar et al. | | 436/53 |
| 5,403,707 A | 4/1995 | Atwood et al. | | 435/5 |
| 5,407,798 A | 4/1995 | Martinelli et al. | | 435/6 |
| 5,411,072 A | 5/1995 | Starck et al. | | 160/84.11 |
| 5,411,863 A | 5/1995 | Miltenyi | | |
| 5,422,075 A | 6/1995 | Saito et al. | | 422/52 |
| 5,433,716 A | 7/1995 | Leopardi et al. | | 604/415 |
| 5,437,841 A * | 8/1995 | Balmer | | 422/102 |
| 5,437,979 A | 8/1995 | Rampal et al. | | 435/6 |
| 5,441,895 A | 8/1995 | Jakubowicz et al. | | |
| 5,453,619 A | 9/1995 | Asselain et al. | | 250/339.12 |
| 5,456,882 A | 10/1995 | Covain | | |
| 5,458,785 A | 10/1995 | Howe et al. | | 210/695 |
| 5,462,715 A | 10/1995 | Koch et al. | | |
| 5,466,574 A | 11/1995 | Liberti et al. | | |
| 5,482,861 A | 1/1996 | Clark et al. | | 436/48 |
| 5,482,864 A | 1/1996 | Knobel | | 436/54 |
| 5,489,532 A | 2/1996 | Charm et al. | | 435/286.1 |
| 5,498,550 A | 3/1996 | Fujiwara et al. | | 436/526 |
| 5,507,410 A | 4/1996 | Clark et al. | | |
| 5,536,475 A | 7/1996 | Moubayed et al. | | 422/101 |
| 5,541,072 A | 7/1996 | Wang et al. | | 435/7.21 |
| 5,565,365 A | 10/1996 | Glass | | 436/526 |
| 5,565,366 A | 10/1996 | Akers, Jr. | | 436/534 |
| 5,567,326 A * | 10/1996 | Ekenberg et al. | | 210/695 |
| 5,567,387 A | 10/1996 | Versluys et al. | | |
| 5,571,479 A | 11/1996 | Koch | | |
| 5,578,270 A | 11/1996 | Reichler et al. | | 422/67 |
| 5,580,524 A | 12/1996 | Forrest et al. | | 422/63 |
| 5,589,350 A | 12/1996 | Bochner | | 435/29 |
| 5,595,913 A | 1/1997 | Lawlor et al. | | 436/17 |
| 5,597,531 A | 1/1997 | Liberti et al. | | 423/57 |
| 5,599,501 A | 2/1997 | Carey et al. | | 422/64 |
| 5,607,766 A | 3/1997 | Berger | | 428/373 |
| 5,620,898 A | 4/1997 | Yaremko et al. | | 436/45 |
| 5,622,831 A | 4/1997 | Liberti et al. | | 435/7.21 |
| 5,628,428 A | 5/1997 | Calhoun et al. | | |
| 5,646,047 A | 7/1997 | Bird et al. | | 436/128 |
| 5,647,994 A | 7/1997 | Tuunanen et al. | | 210/695 |
| 5,658,532 A | 8/1997 | Kurosaki et al. | | |
| 5,665,558 A | 9/1997 | Frame et al. | | |
| 5,681,478 A | 10/1997 | Lea et al. | | 210/695 |
| 5,702,950 A | 12/1997 | Tajima | | 436/49 |
| 5,705,062 A | 1/1998 | Knobel | | |
| 5,741,708 A | 4/1998 | Carey et al. | | 436/49 |
| 5,789,167 A | 8/1998 | Konrad | | 435/6 |
| 5,795,470 A * | 8/1998 | Wang et al. | | 210/222 |
| 5,827,478 A | 10/1998 | Carey et al. | | 422/64 |
| 5,834,197 A | 11/1998 | Parton | | 435/6 |
| 5,837,144 A | 11/1998 | Bienhaus et al. | | 210/695 |
| 5,843,312 A | 12/1998 | Manz et al. | | 210/635 |
| 5,849,247 A | 12/1998 | Uzan et al. | | 422/65 |
| 5,869,328 A | 2/1999 | Antoci et al. | | |
| 5,877,035 A | 3/1999 | Fujino et al. | | 438/16 |
| 5,885,529 A | 3/1999 | Babson et al. | | 422/65 |
| 5,885,530 A | 3/1999 | Babson et al. | | 422/65 |
| 5,888,758 A | 3/1999 | Wu | | 435/28 |
| 5,888,835 A | 3/1999 | Bushnell et al. | | 436/526 |
| 5,895,631 A | 4/1999 | Tajima | | 422/101 |
| 5,897,783 A | 4/1999 | Howe et al. | | 210/695 |
| 5,902,548 A | 5/1999 | Watts et al. | | |
| 5,910,122 A | 6/1999 | D'Angelo | | 600/573 |
| 5,915,583 A | 6/1999 | Cloonan et al. | | |
| 5,919,706 A | 7/1999 | Tajima | | 436/54 |
| 5,922,284 A | 7/1999 | Kinoshita et al. | | 422/68.1 |
| 5,932,299 A | 8/1999 | Katoot | | 427/508 |
| D414,562 S | 9/1999 | Tajima | | 24/222 |
| 5,948,363 A | 9/1999 | Gaillard | | |
| 5,952,233 A | 9/1999 | Pellet et al. | | 436/6 |
| 5,959,221 A * | 9/1999 | Boyd et al. | | 73/864.24 |
| 5,976,369 A | 11/1999 | Howe et al. | | |
| 5,985,153 A | 11/1999 | Dolan et al. | | 210/695 |
| 5,985,671 A | 11/1999 | Leistner et al. | | 436/49 |
| 5,993,665 A | 11/1999 | Terstappen et al. | | 210/695 |
| 6,001,573 A | 12/1999 | Roelant | | 435/6 |
| 6,006,800 A | 12/1999 | Nakano | | 141/130 |
| 6,008,010 A | 12/1999 | Greenberger et al. | | 435/41 |
| 6,013,188 A | 1/2000 | Terstappen et al. | | 210/695 |
| 6,020,211 A | 2/2000 | Tuunanen | | 436/526 |
| 6,040,192 A | 3/2000 | Tuunanen | | 436/177 |
| 6,043,205 A | 3/2000 | Hoshiko et al. | | 510/161 |
| 6,063,260 A | 5/2000 | Olesen et al. | | 205/793 |
| 6,065,605 A | 5/2000 | Korpela et al. | | |
| 6,066,297 A | 5/2000 | Torti et al. | | |
| 6,074,609 A | 6/2000 | Gavin et al. | | 422/99 |
| 6,096,554 A | 8/2000 | Tajima | | 436/49 |
| 6,100,079 A | 8/2000 | Tajima | | 435/239 |
| 6,100,094 A | 8/2000 | Tajima | | 436/54 |
| 6,114,292 A | 9/2000 | Hoshiko et al. | | 510/161 |
| 6,117,398 A | 9/2000 | Bienhaus et al. | | 422/101 |

| | | | |
|---|---|---|---|
| 6,123,903 A | 9/2000 | Tajima | 422/52 |
| 6,124,142 A | 9/2000 | Fujino et al. | 438/18 |
| 6,133,037 A | 10/2000 | Tajima | 436/49 |
| 6,136,182 A | 10/2000 | Dolan et al. | 210/94 |
| 6,143,250 A | 11/2000 | Tajima | 422/102 |
| 6,143,578 A | 11/2000 | Bendele et al. | 436/526 |
| 6,146,838 A | 11/2000 | Williams et al. | 435/7.2 |
| 6,150,182 A | 11/2000 | Cassaday | 436/526 |
| 6,174,668 B1 | 1/2001 | Cummins et al. | 435/6 |
| 6,187,270 B1 | 2/2001 | Schmitt et al. | |
| 6,193,892 B1 | 2/2001 | Krueger et al. | 210/695 |
| 6,225,061 B1 | 5/2001 | Becker et al. | 435/6 |
| 6,225,126 B1 | 5/2001 | Cohen et al. | 436/69 |
| 6,225,128 B1 | 5/2001 | White | 436/77 |
| 6,231,814 B1 | 5/2001 | Tajima | 422/101 |
| 6,232,124 B1 | 5/2001 | Selinfreund | 436/20 |
| 6,249,345 B1 | 6/2001 | Kraack et al. | |
| 6,255,051 B1 | 7/2001 | Hammond et al. | 435/6 |
| 6,268,209 B1 | 7/2001 | Pierson et al. | 435/287.9 |
| 6,277,332 B1 | 8/2001 | Sucholeiki | 422/128 |
| 6,291,249 B1 | 9/2001 | Mahant et al. | 436/177 |
| 6,328,934 B1 | 12/2001 | Ljung et al. | 422/119 |
| 6,331,277 B2 | 12/2001 | Tajima | 422/100 |
| 6,332,705 B1 * | 12/2001 | Herz et al. | 366/208 |
| 6,333,008 B1 | 12/2001 | Leistner et al. | |
| 6,335,166 B1 | 1/2002 | Ammann et al. | 435/6 |
| 6,337,053 B1 | 1/2002 | Tajima | 422/102 |
| 6,346,408 B1 | 2/2002 | Chueh | 435/238 |
| 6,368,872 B1 | 4/2002 | Juranas | 436/180 |
| 6,370,942 B1 | 4/2002 | Dunfee et al. | 73/37 |
| 6,372,183 B1 | 4/2002 | Akong et al. | 422/63 |
| 6,372,185 B1 | 4/2002 | Shumate et al. | 422/100 |
| 6,375,898 B1 | 4/2002 | Ulrich | |
| 6,396,584 B1 | 5/2002 | Taguchi et al. | 356/436 |
| 6,409,925 B1 | 6/2002 | Gombinsky et al. | 210/695 |
| 6,444,171 B1 | 9/2002 | Sakazume et al. | 422/65 |
| 6,447,729 B1 | 9/2002 | Tuunanen | 422/101 |
| 6,448,092 B1 | 9/2002 | Tuunanen | 436/526 |
| 6,455,325 B1 | 9/2002 | Tajima | 436/526 |
| 6,461,808 B1 | 10/2002 | Bodner et al. | 435/4 |
| 6,468,810 B1 | 10/2002 | Korpela | 436/526 |
| 6,470,279 B1 | 10/2002 | Samsoondar | 702/28 |
| 6,471,917 B1 | 10/2002 | Velkovska et al. | 422/100 |
| 6,482,328 B1 | 11/2002 | Davidson et al. | 210/695 |
| 6,500,343 B2 | 12/2002 | Siddiqi | |
| 6,509,193 B1 | 1/2003 | Tajima | |
| 6,517,783 B2 | 2/2003 | Horner et al. | 422/102 |
| 6,537,505 B1 | 3/2003 | LaBudde et al. | 422/103 |
| 6,543,515 B2 | 4/2003 | Hummell et al. | 156/556 |
| 6,551,833 B1 | 4/2003 | Lehtinen et al. | |
| 6,569,204 B1 | 5/2003 | Aldecoa | 623/23.51 |
| 6,572,778 B2 | 6/2003 | Sterman et al. | 210/695 |
| 6,573,088 B2 | 6/2003 | Gemmell et al. | 435/286.4 |
| 6,579,453 B1 | 6/2003 | Bächler et al. | 210/222 |
| 6,597,176 B2 | 7/2003 | Simmonds et al. | 324/326 |
| 6,602,422 B1 | 8/2003 | Miltenyi et al. | 210/695 |
| 6,605,213 B1 | 8/2003 | Ammann et al. | |
| 6,610,186 B1 | 8/2003 | Mayer et al. | 204/451 |
| 6,649,419 B1 | 11/2003 | Anderson | |
| 6,660,159 B1 | 12/2003 | Terstappen et al. | |
| 6,672,458 B2 | 1/2004 | Hansen et al. | |
| 6,691,748 B1 | 2/2004 | Tajima | |
| 6,723,237 B1 | 4/2004 | Tajima | |
| 6,764,859 B1 | 7/2004 | Kreuwel et al. | |
| 6,776,174 B2 * | 8/2004 | Nisson et al. | 134/104.4 |
| 6,790,366 B2 | 9/2004 | Terstappen et al. | |
| 6,805,840 B1 | 10/2004 | Tajima | |
| 6,884,357 B2 | 4/2005 | Siddiqi | |
| 2001/0007312 A1 | 7/2001 | Siddiqi | 210/695 |
| 2001/0007770 A1 | 7/2001 | Tajima | 436/47 |
| 2001/0016178 A1 | 8/2001 | Acosta et al. | 422/100 |
| 2002/0008053 A1 | 1/2002 | Hansen et al. | 209/8 |
| 2002/0048534 A1 | 4/2002 | Storek et al. | 422/99 |
| 2002/0048821 A1 | 4/2002 | Storek et al. | 436/174 |
| 2003/0012699 A1 | 1/2003 | Moore et al. | 422/100 |
| 2003/0049171 A1 | 3/2003 | Tamura et al. | 422/64 |
| 2003/0215361 A1 | 11/2003 | Jang | |
| 2004/0004043 A1 | 1/2004 | Terstappen et al. | |
| 2004/0029291 A1 | 2/2004 | Franzreb et al. | |
| 2004/0047765 A1 | 3/2004 | Gordon et al. | |
| 2004/0265173 A1 | 12/2004 | Matsumoto et al. | |
| 2004/0265903 A1 | 12/2004 | Mueller et al. | |
| 2005/0013741 A1 | 1/2005 | a' Brassard | |
| 2005/0013746 A1 * | 1/2005 | Lee et al. | 422/102 |
| 2005/0047963 A1 | 3/2005 | Safar et al. | |
| 2005/0084423 A1 | 4/2005 | Zarowitz et al. | |

FOREIGN PATENT DOCUMENTS

| | | |
|---|---|---|
| EP | 0831329 | 3/1998 |
| EP | 1037050 | 9/2000 |
| JP | 04-336773 | 11/1992 |
| JP | 2002-243636 | 8/2002 |
| JP | 2004-077418 | 3/2004 |
| WO | WO 95/00247 | 1/1995 |
| WO | WO 01/28701 * | 2/2001 |
| WO | WO 01/28701 * | 4/2001 |
| WO | WO 02/44725 A1 | 6/2002 |
| WO | WO 03/090877 | 11/2003 |

OTHER PUBLICATIONS

"Chemilumitteszenz . . . bringt Licht ins Labor," Publication of Ciba-Corning Diagnostics GmbH, 1996, pp. 1-11, Presented at the 4th International Bioluminescence and Chemiluminescence Symposium, Freiburg, Germany, Sep. 1986. Original German language publication and English translation.

Doyle et al., "Self-Assembled Magnetic Matrices for DNA Separation Chips," Science vol. 295, Mar. 22, 2002 at. 2297.

European Search Report for European Patent Application for EP 0638809 A2, Dec. 9, 1996.

Guesdon et al., "Magnetic Solid Phase Enzyme-Immunoassay," Immunochemistry, 1977, vol. 14, pp. 443-447.

Landon, "Magneitsable Particles in Immunochemistry," 1982, Technical Publication of Worldwide Technical Marketing, Corning Medical, Medfield, Massachusetts, pp. 1-5. (Please note: Applicant best estimates 1982 as the year when this document became publicly available.).

McNicol et al., "Automation of Dupont's Chromium Dioxide Magnetic Particle Based Immunoassays," pp. 1-19, presented Apr. 13-14, 1988, in Savannah, Georgia, at the Oakridge Meeting of the Association for Clinical Chemists.

Ng et al., "Performance of Five Thyroid-Function Tests by Radioimmunoassays with Antibodies Attached to Paramagnetic Micro-Particles," Clinical Chemistry, 1985, vol. 31 No. 1, pp. 87-90.

Nye et al., "Solid-Phase, Magnetic Particle Radioimmunoassay," Clinica Chimica Acta, 1976, vol. 69, pp. 387-396.

Piran et al., "Immunochemiluminometric Assay of Creatine Kinase MB with a Monoclonal Antibody to the MB Isoenzyme," Clinical Chemistry, 1987, vol. 33 No. 9, pp. 1517-1520.

Sturgess et al., "Chemiluminescent Labeled-Antibody Assay for Thyroxin in Serum, with Magnetic Separation of the Solid-Phase," Clinical Chemistry, 1986, vol. 32 No. 3, pp. 532-535.

Weeks et al. "Chemiluminescence Immunoassay," Journal of Clinical Immunoassay, Spring 1984, vol. 7, No. 1, pp. 82-89.

International Search Report for International Application No. PCT/US2005/019997, mailed Dec. 7, 2005 (8 pages).

Written Opinion of the International Searching Authority for International Application No. PCT/US2005/019997, mailed Dec. 7, 2005 (8 pages).

* cited by examiner

TAPERED CUVETTE AND METHOD OF COLLECTING MAGNETIC PARTICLES

TECHNICAL FIELD OF THE INVENTION

The present invention relates generally to cuvettes for holding samples and more specifically to cuvettes for holding samples to be analyzed in an automated immunoassay device utilizing magnetic particles, and methods thereof.

BACKGROUND OF THE INVENTION

Cuvettes are typically used for holding samples, such as aliquots of a reaction mixture, an environmental sample, blood, urine or fractions thereof, for use in medical diagnostic test procedures requiring optical measurements. Immobilization, capture or recovery of an analyte of interest in the sample may be accomplished using magnetic particles.

A goal of medical laboratories is to enhance laboratory efficiency by automating clinical diagnostic test procedures, such as immunoassay, and increasing throughput. Automated clinical diagnostic devices analyze a greater number of samples than manual assays in a given timeframe, while at the same time minimize the number of interactions between laboratory personnel, the samples, and the clinical diagnostic instrument. Clinical samples, usually available in small quantities, and the reagents used in clinical diagnostic procedures are costly. Automated assays utilizing magnetic particle must capture substantially all of the magnetic particles in a sample to collect and analyze the analyte of interest.

Therefore, it would be desirable to provide a cuvette for use in an automated clinical diagnostic device that accommodates a small volume of fluid, such as the sample and reagent fluids, and captures, washes, and resuspends the magnetic particles within the small volume of fluid.

SUMMARY OF THE INVENTION

The invention described herein features a vessel for use in automated clinical sample analysis, for example, automated immunoassay.

In one aspect, the invention relates to a device, such as a vessel or cuvette including an open top, a closed bottom, and at least four sides. At least two of the four sides are opposite to each other. In one embodiment, the opposite sides are flat and symmetrical. At least two of the sides of the vessel are tapered from the open top to the closed bottom of the vessel. The vessel has a larger interior cross-sectional area at the open top and a smaller interior cross-sectional area at the closed bottom. The tapered sides of the vessel are tapered at an angle of about 5.82 degrees relative to the normal. In one embodiment, the closed bottom is convex.

In one embodiment of the invention, the combined surface area of the pair of opposite sides is greater than the combined surface area of the other sides. The ratio of the combined surface area of the opposite sides compared to the combined surface area of the other sides is in the range of about 4:1 to about 2:1, preferably about 3:1. In one embodiment of the invention, the interior cross-sectional area of the vessel is greater at the top of the vessel than at the bottom of the vessel.

In one embodiment of the invention, at least one pair of opposite sides is composed of a substantially transparent material.

In one embodiment of the invention, the vessel also contains a flange positioned at the open top of the vessel to hold the vessel in an upright and level position in an analytical instrument. In another embodiment of the invention, the vessel comprises two flanges that extend 1.33 mm outward from the top of the vessel on opposite sides of the vessel. In another embodiment, the flange extends substantially the same distance from the sides of the vessel on all sides.

In one embodiment of the invention, the vessel also contains a projection on an exterior surface of one side of the vessel. The projection extends from the flange and along the side of the vessel. In one embodiment of the invention, the vessel is stacked with like vessels. The projections on the sides of the vessel serve to separate the vessels when in a stacked configuration. The exterior surface of a first vessel and the interior surface of a second vessel define a space between the first and second vessels of at least 4.5 mm. In one embodiment, the space between the vessels is substantially equivalent to the depth of the projection.

In another aspect, the invention relates to a vessel cartridge for loading vessels in an automated clinical diagnostic device. The vessel cartridge comprises a plurality of vessels. The exterior surface of a first vessel and the interior surface of a second vessel define a space between the first and second vessels. The space between the first and second vessels is at least 4.5 mm. In another embodiment, the space between the first and second vessels is defined by a projection on the surface of the first vessel. The vessel cartridge may be loaded onto and automatically fed into an automated clinical diagnostic device.

In another aspect, the invention relates to a method for collecting magnetic particles comprising the steps of providing a magnet and a vessel containing magnetic particles in a fluid, attracting the magnetic particles to the magnet, and moving the magnetic particles with the magnet out of the fluid. In one embodiment, the method further comprises the step of removing the fluid from the vessel after the magnetic particles have been moved out of the fluid. In one embodiment, the magnet is moved to move the magnetic particles out of the fluid. In another embodiment, the vessel is moved to move the magnetic particles out of the fluid.

In another aspect, the invention relates to a device for washing magnetic particles in a vessel. The device includes a holder comprising a lumen or receiving the vessel. The holder includes a straight side and a sloped side opposite to the straight side. The straight side includes a lever arm that is reciprocally moveable from a position within the holder lumen to a position outside the holder lumen. The lever arm is biased toward the holder lumen to retain the vessel in the holder lumen. In one embodiment of the invention, the lever arm further includes a spring. In another embodiment of the invention, the device further includes a magnet.

BRIEF DESCRIPTION OF THE FIGURES

These and other aspects of this invention will be readily apparent from the detailed description below and the appended drawings, which are meant to generally illustrate and not to limit the invention, and in which.

DESCRIPTION OF THE INVENTION

The invention, described herein, relates to a vessel, such as an optical cuvette, for use in clinical analytical instruments, including immunoassay instruments. The embodiments of the invention described below have the following common features: a vessel including an open top and a closed bottom, at least four sides, and at least two of the four sides are tapered. The sides also include at least two sides that are opposite to each other and are flat. The tapered sides are tapered from the open top to the closed bottom.

In general, the vessel is a cuvette that serves as a reservoir for washing, rinsing, or otherwise manipulating magnetic particles, such as beads, in a fluid medium such as a suspension or a solution including analytical reagents.

Figure 1:
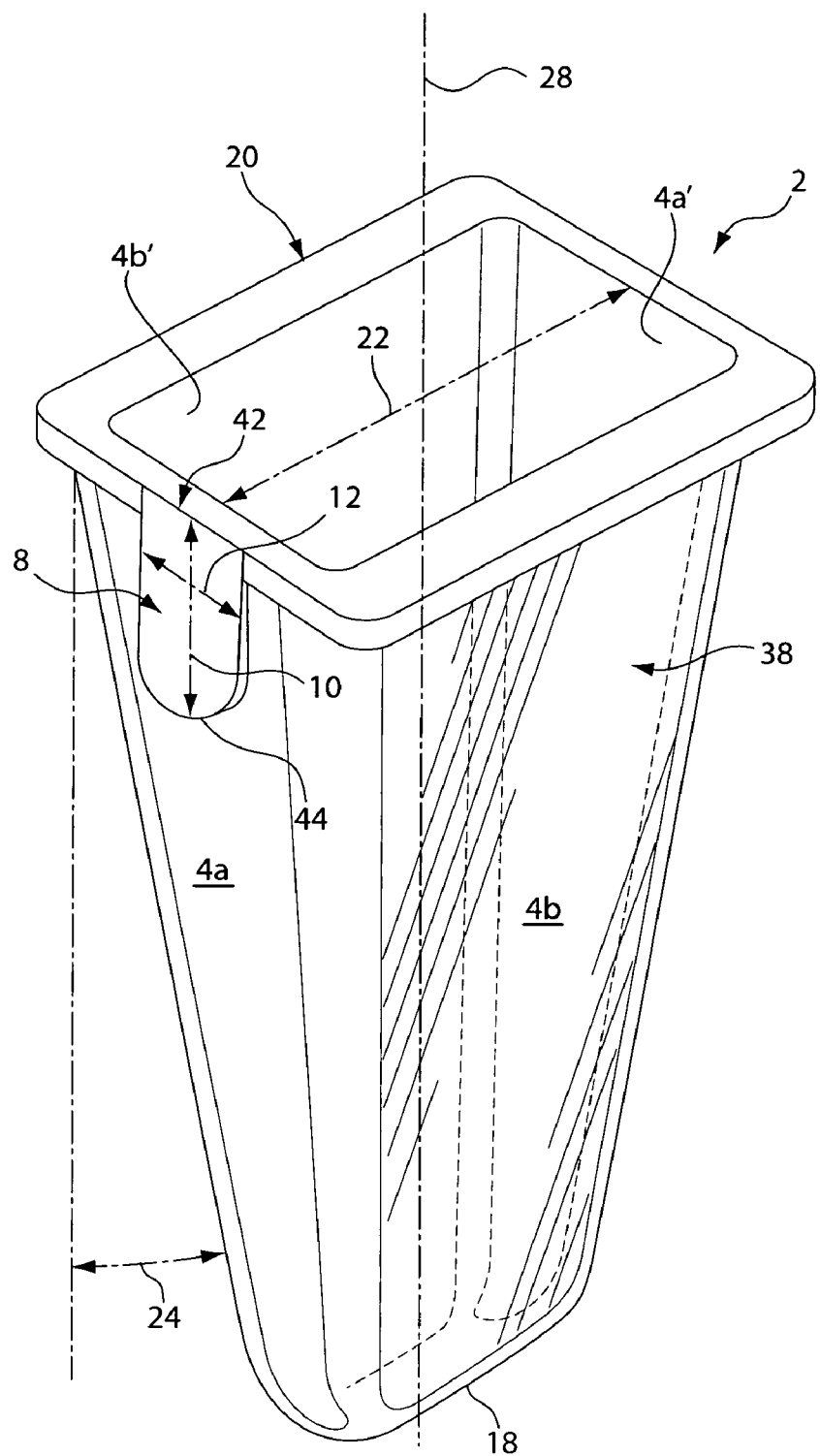
FIG. 1 is a schematic front perspective view of a tapered vessel according to an illustrative embodiment of the invention.

FIG. 1 is a schematic front perspective view of a tapered vessel according to an illustrative embodiment of the invention. Referring to FIG. 1, the illustrative vessel 2 has an open top 20 and a closed bottom 18. The vessel 2 has at least four sides 4a, 4a', 4b, 4b' and at least two of the at least four sides 4a, 4a', 4b, 4b' oppose each other. These two opposite sides, for example the two opposite sides 4b, 4b', form a pair of opposite sides. The vessel 2 may have more than four sides, such as 5, 6, 7, 8 or more.

With continued reference to FIG. 1, the pair of opposite sides, for example 4b, 4b', are flat, meaning the entire surface of each side 4b, 4b' is substantially planar and does not bend or arc outside the plane. In another embodiment of the invention, two pairs of opposite sides 4a, 4a', 4b, 4b' are flat. In another embodiment, the vessel may have more than four sides (not shown) and more than two pairs of opposite sides 4a, 4a', 4b, 4b' are flat.

With continued reference to FIG. 1, in one embodiment, one pair of opposite sides includes an optical window in each side of the pair of sides for use in an optical measurement instrument, for example, a spectrophotometer. The pair of optical sides including an optical window, for example 4b, 4b', are symmetrical, meaning the sides 4b, 4b' have identical widths at the top 20 of the vessel 2 and at the bottom 18 of the vessel 2, respectively, and the sides 4b, 4b' have identical taper angles 24 from the top 20 of the vessel 2 to the bottom 18 of the vessel 2. The taper angles 24 of the sides 4a, 4a', 4b, 4b' are measured from the top 20 of the vessel 2, parallel to and relative to the vertical axis 28 of the vessel 2 and range from 4 to 10 degrees. In one embodiment, each side 4a, 4a', 4b, 4b' forms an isosceles trapezoid.

Referring still to FIG. 1, in one embodiment of the invention, the surface area of the pair of sides 4b, 4b' including an optical window is greater than the surface area of the sides 4a, 4a' that do not include optical windows. The ratio of the surface area of the sides 4b, 4b' including an optical window to the surface area of the sides 4a, 4a' that do not include an optical window is in the range of about 4:1 to about 2:1, preferably 3:1. In another embodiment according to the invention, the surface area of each side 4a, 4a', 4b, 4b' of the vessel 2 is equal (not shown).

The sides not including an optical window, for example 4a, 4a', serve as magnetic particle engagement sites during magnetic particle wash procedures. For example, the particle engagement sides 4a, 4a', according to one embodiment, are flat, more narrow than the sides 4b, 4b' having optical windows, and form one or more pairs of opposite sides. During a magnetic wash procedure, the flat surface of the particle engagement sides 4a, 4a' provides a uniform surface for a magnet (not shown) to engage the vessel 2, and thereby creates a uniform magnetic flux density across the entire surface of the particle engagement sides 4a, 4a'. When the magnet is engaged with the particle engagement sides 4a, 4a' of the vessel 2, magnetic particles are attracted to the magnet and accumulate uniformly along the flat surface of the particle engagement sides 4a, 4a'. The advantage of a flat surface compared to a curved or arched surface is that a curved or arched particle engagement surface engages a magnet at only one central point of engagement and the magnet exerts a very strong flux density at this point. Surfaces adjoining this central point of magnet engagement experience a reduced magnetic flux density. As a result of the variable magnetic flux density, the magnetic particles congregate and stack upon one another at the point of greatest flux density. When particles stack, fewer magnetic particles are pulled out of the solution and a greater number of magnetic particles are destroyed, damaged, or lost during the magnetic wash procedure. Particle stacking also traps contaminants and other waste materials between particles, resulting in inadequate particle washing.

With continued reference to FIG. 1, in one embodiment of the invention, the closed bottom 18 of the vessel 2 may have various shapes, including, for example, convex, concave or flat, relative to the interior volume of the vessel 2. The corners between the closed bottom 18 and the sides 4a, 4a', 4b, 4b' of the vessel 2 may have various shapes, including, for example, rounded or square. The closed bottom 18 of the vessel 2 has a surface area that is less than the surface area of the open top 20 of the vessel 2.

Referring still to FIG. 1, the sides 4a, 4a', 4b, 4b' of the vessel 2 are tapered from the open top 20 of the vessel 2 to the closed bottom 18 of the vessel 2. The sides 4a, 4a', 4b, 4b' are tapered such that the interior cross-sectional area 22 of the vessel 2, measured in a plane perpendicular to the vertical axis 28 of the vessel 2, is greater at the top 20 of the vessel 2 than at the bottom 18 of the vessel 2. The sides 4a, 4a', 4b, 4b' of the vessel 2 are tapered at an angle 24 of about 5 degrees to about 7 degrees relative to the vertical axis 28 of the vessel 2, preferably about 5.8 degrees.

The tapered sides 4a, 4a', 4b, 4b' of the vessel 2 facilitate attraction of the magnetic particles to one side 4a, 4a', 4b, 4b' of the vessel 2 by a magnet, for example, a magnet composed of Neodymium, in a clinical instrument used to separate magnetic particles from the fluid medium in which they are suspended. For example, a magnet (not shown) attracts the magnetic particles in the narrow bottom 18 of the vessel 2, where the magnetic particles travel a shorter distance. The magnet is then moved vertically along the side 4a, 4a', 4b, 4b' of the vessel 2, carrying with it the magnetic particles. In a preferred embodiment, collection of magnetic particles occurs along the narrow, particle engagement side 4a, 4a' of the vessel 2 illustrated in FIG. 1. Collecting the magnetic particles along the narrow width of the flat particle engagement side 4a, 4a' of the vessel 2 requires less time for particle separation and results in fewer lost particles than in a cylindrical vessel that is cylindrical in shape and has curved or bowed sides.

The tapered sides 4a, 4a', 4b, 4b' of the vessel 2 also facilitate optical reading of a fluid sample contained within the vessel 2. In a preferred embodiment, the optical side 4b, 4b' of the vessel 2 is used for optical reading. The optical side 4b, 4b' of the vessel 2 is wider than the particle engagement side 4a, 4a' of the vessel. In combination with the adjacent narrow, particle engagement side 4a, 4a', the tapered vessel 2 provides a large surface area on the optical side 4b, 4b' of the vessel 2 for optical detection, requiring a small volume of fluid for analysis.

Referring still to FIG. 1, in one embodiment, the vessel 2 has a liquid volume of about 0 uL to about 1300 uL, preferably about 450 uL to about 1340 uL, and more preferably about 450 uL.

With continued reference to FIG. 1, in one embodiment according to the invention, the vessel 2 includes projections 8 on the exterior surface 38 of opposite sides 4a, 4a', 4b, 4b' at the top 20 of the vessel 2. In one embodiment, the vessel 2 contains projections 8 on one pair of opposite sides 4a, 4a', 4b, 4b'. In another embodiment, the vessel 2 contains projections 8 on more than one pair of opposite sides 4a, 4a', 4b, 4b'. In a preferred embodiment, illustrated in FIG. 1, the vessel 2 contains projections 8 on the pair of narrow, particle engagement sides 4a, 4a'.

Figure 2:
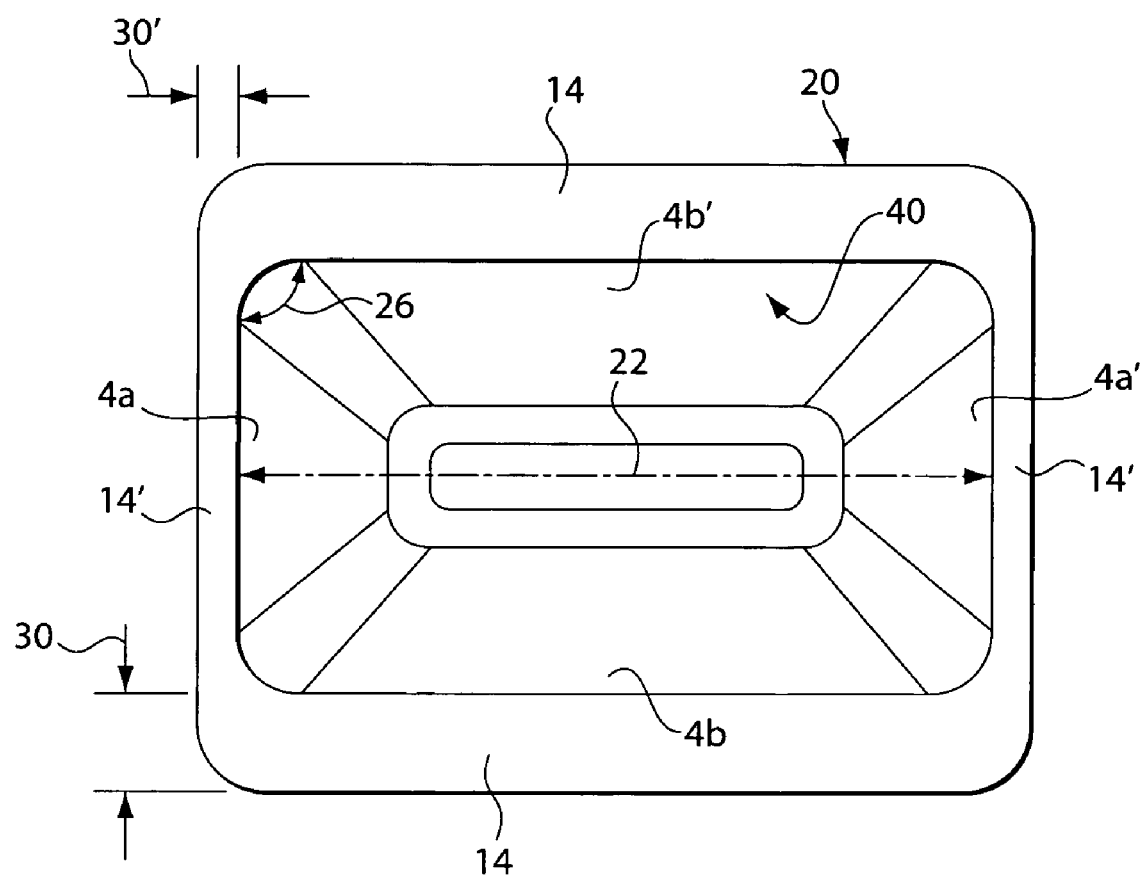
FIG. 2 is a schematic top view of a tapered vessel according to an illustrative embodiment of the invention.

FIG. 2 is a schematic top view of a tapered vessel. The exemplary vessel 2 includes a flange 14, 14' around the perimeter of the open top 20, extending a distance 30, 30', respectively, from the interior surface 40 of the sides 4a, 4a', 4b, 4b' of the vessel 2. In one embodiment, the flange 14, 14' extends in a plane perpendicular to the vertical axis 28 of the vessel 2. In one embodiment, the width of the flange 14, 14' is substantially equal on each side 4a, 4a', 4b, 4b' of the vessel 2 and extends a distance 30, 30', respectively, of about 1 mm to about 2 mm from the interior surface 40 of the sides 4a, 4a', 4b, 4b' of the vessel 2 on the top 20 of the vessel 2, preferably about 1.5 mm. In another embodiment, the flange 14 on the optical sides 4b, 4b' of the vessel 2 extends an equal distance 30, but a distance unequal to the distance 30' the flange 14' extends on the particle engagement sides 4a, 4a'. In another embodiment, the flange 14, 14' extends an unequal distance 30, 30' on each side 4a, 4a', 4b, 4b'. In a preferred embodiment, the flange 14 on the optical sides 4b, 4b' extends a distance 30 of about 0.5 mm to about 2 mm, preferably about 0.5 mm and the flange 14' on the particle engagement sides 4a, 4a' extends a distance 30' of about 0.5 mm to about 2 mm, preferably about 0.5 mm. The flange 14, 14' serves to hold the vessel 2 in an upright and level position. In another embodiment, the vessel 2 does not have a flange.

Referring still to FIG. 2, in one embodiment of the invention, each of the inner corners 26 of the vessel 2, where the optical sides 4b, 4b' and the particle engagement sides 4a, 4a' meet form an angle in the range of about 70 degrees to about 110 degrees, preferably about 80 degrees to about 100 degrees, and more preferably 90 degrees. Right angled corners maximize the internal volume of the vessel 2 while minimizing, for example, the length of the vessel 2.

Figure 3:
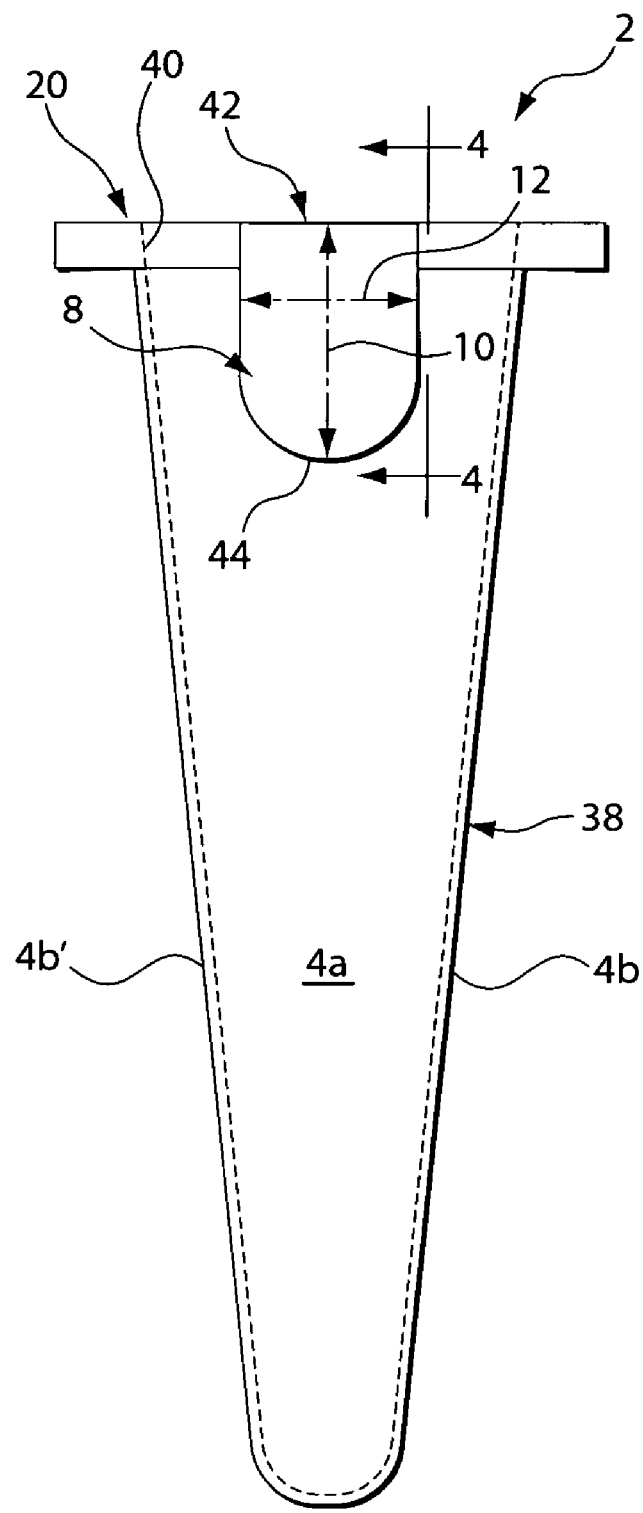
FIG. 3 is a schematic side view of a tapered vessel including a projection according to an illustrative embodiment of the invention.

FIG. 3 is a schematic side view of a tapered vessel including a projection according to an illustrative embodiment of the invention. Referring to FIG. 3, according to one embodiment of the invention, the vessel 2 contains a projection 8 that extends from the top 20 of the vessel 2 and along the side 4a, 4a' of the vessel 2 a length 10 of about 4 mm to about 7 mm, preferably about 5 mm. The projection 8 projects from the side 4a, 4a' of the vessel 2 a width 12 of about 3 mm to about 4 mm, preferably about 3.5 mm. In another embodiment, the width 12 of the projection 8 extends the entire width of the side 4a, 4a', 4b, 4b' of the vessel 2.

With continued reference to FIG. 3, in one embodiment, the projection 8 is centered on the side 4a, 4a', 4b, 4b' of the vessel with respect to the top 20 surface of the vessel 2. The bottom 44 of the projection 8 may have a variety of shapes, including, for example, rounded, pointed, or flat.

Figure 4:
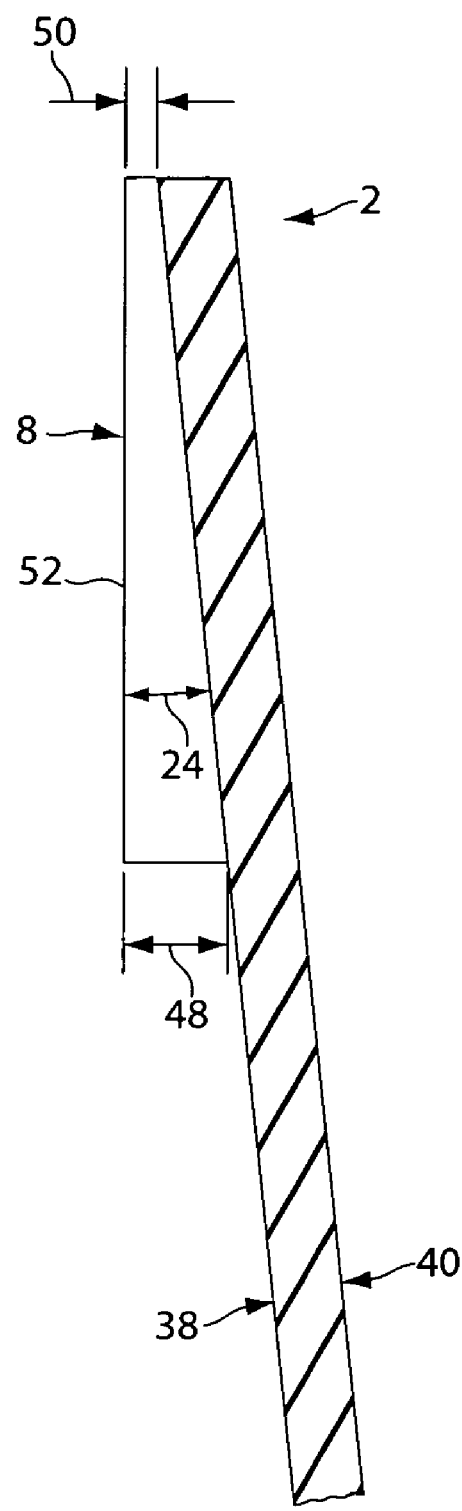
FIG. 4 is a schematic cross-sectional side view of a projection on a side of a tapered vessel according to an illustrative embodiment of the invention.

FIG. 4 is a schematic cross-sectional side view of a projection on a side of a tapered vessel according to an illustrative embodiment of the invention. The top width 50 of the exemplary projection 8 is equal to the width 30, 30' of the corresponding flange 14, 14' along the corresponding side 4a, 4a', 4b, 4b' of the vessel 2. In another embodiment, the top width 50 of the projection 8 is greater or less than the width 30, 30' of the corresponding flange 14, 14' along the corresponding side 4a, 4a', 4b, 4b' of the vessel by an amount in the range of about 0.1% to about 30%.

With continued reference to FIG. 4, according to one embodiment of the invention, the exterior surface 52 of the projection 8 is substantially parallel to the vertical axis 28 of the vessel 2. The angle between the exterior surface 52 of the projection 8 and the exterior surface 38 of the side 4a, 4a', 4b, 4b' of the vessel 2 is substantially equal to the taper angle 24 of the side 4a, 4a', 4b, 4b' of the vessel 2 relative to the vertical axis 28 of the vessel 2.

The vessel 2, according to one embodiment of the invention, is composed of a substantially translucent polymer or other substance known to those in the field with similar optical qualities. The polymer may be for example polypropylene, polyethylene, or polytetrafluoroethylene.

Figure 5:
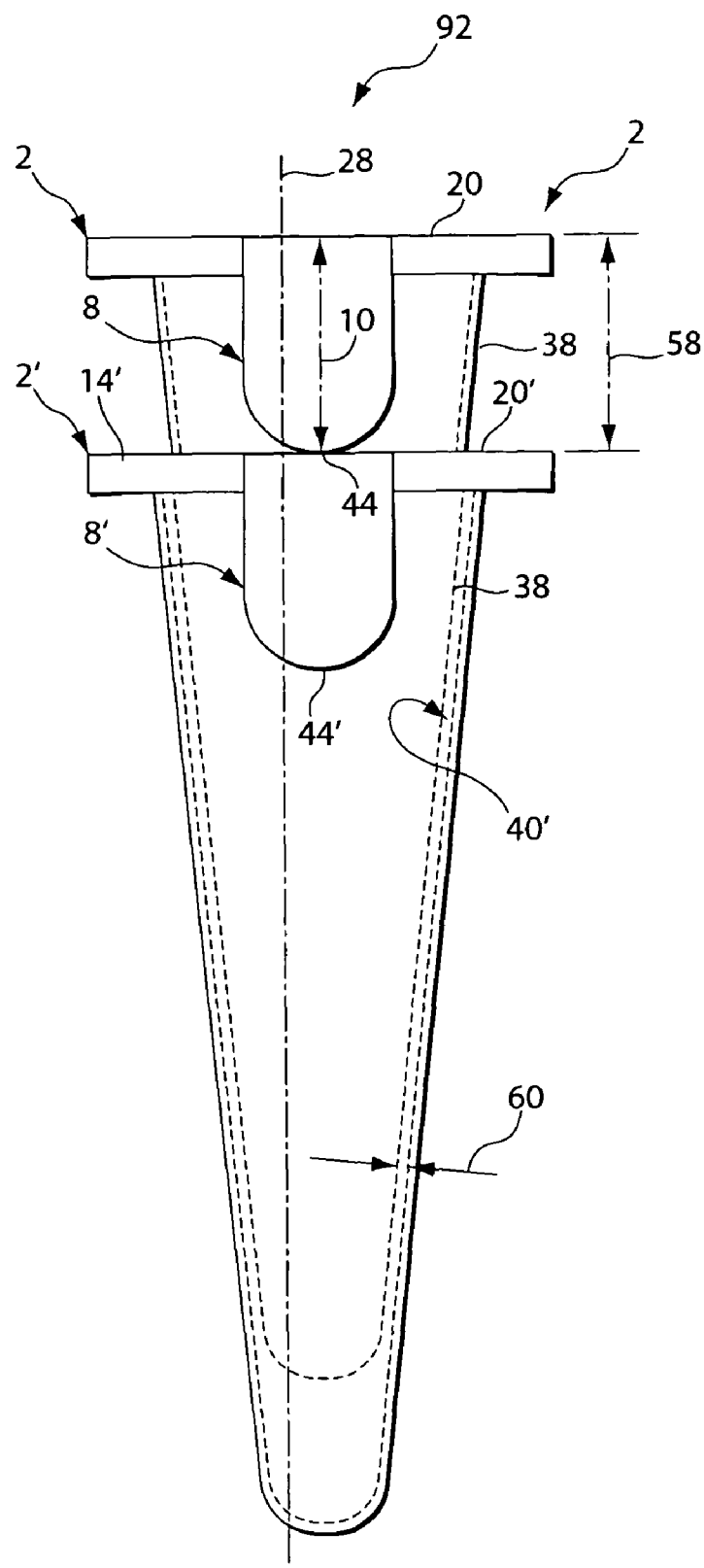
FIG. 5 is a schematic side view of two stacked tapered vessels according to an illustrative embodiment of the invention.

FIG. 5 is a schematic drawing of two stacked tapered vessels according to an illustrative embodiment of the invention. The illustrative vessel 2 is stackable with like vessels 2. A first vessel 2 is inserted, along the vertical axis 28 of the vessel 2, into a second vessel 2'. When in a stacked configuration, in one embodiment, the bottom 44 of the projection 8 of the first vessel 2 is supported on the top 20 of the second vessel 2'. In another embodiment, the first vessel 2 is supported on the flange 14' of the second vessel 2'. The tops 20, 20' of the vessels 2, 2', respectively, are separated by a distance 58 substantially equal to the length 10 of the projection 8. The distance 58 between the first vessel 2 and the second vessel 2' is about 4 mm to about 5 mm, preferably 4.2 mm.

With continued reference to FIG. 5, according to one embodiment of the invention, when the vessels 2, 2' are in a stacked configuration, the exterior surface 38 of the first vessel 2 is separated from the interior surface 40' of the second vessel 2' by a separation gap 60. The separation gap 60 between the first vessel 2 and the second vessel 2' is determined by the length 10 of the projection 8. Increasing the length 10 of the projection 8 increases the separation gap 60 between the vessels 2, 2'. Decreasing the length 10 of the projection 8 decreases the separation gap 60 between the vessels 2, 2'.

The separation gap 60 between the first vessel 2 and the second vessel 2' is advantageous because the gap 60 prevents the surfaces 38, 40' of the vessels 2, 2' from touching and being scratched. Scratches on the sides 4a, 4a', 4b, 4b' of the vessel 2 interfere with the transmission of an analytical beam of light through the two opposite optical sides 4b, 4b' and through a fluid sample contained by the vessel 2. Interference with light transmission alters the characteristics of a sample measured by analytical instruments that use light, for example, spectrophotometers.

With continued reference to FIG. 5, in one embodiment, a plurality of vessels 2 are stacked to form a vessel cartridge 92 for loading vessels 2 in an automated clinical diagnostic device. The vessel cartridge 92 comprises a plurality of vessels 2, with the exterior surface 38 of a first vessel 2 and the interior surface 40' of a second vessel 2' defining a gap 60 between the first vessel 2 and the second vessel 2'. The gap 60 between the first vessel 2 and the second vessel 2' is in the range of about 0 mm to about 0.25 mm, preferably about 0.1 mm. The gap 60 between the first vessel 2 and the second vessel 2' is defined by the projection 8 on the exterior surface 38 of the first vessel 2. The vessel cartridge 92 contains 10 to 20 vessels 2, preferably 15 vessels 2.

Referring still to FIG. 5, by stacking the vessel 2 in the vessel cartridge 92, a greater number of vessels 2 may be arranged in a smaller volume than the same number of vessels not stacked. The vessel cartridge 92 loads a plurality of vessels 2 onto a clinical analytical instrument in one step. A vessel loader (not shown) located on the clinical analytical instrument automatically feeds one vessel 2 into the clinical analytical instrument at a time as needed. The vessel cartridge 92 also maintains the sterility of interior vessels during storage and requires less operator interaction.

Figure 6A:
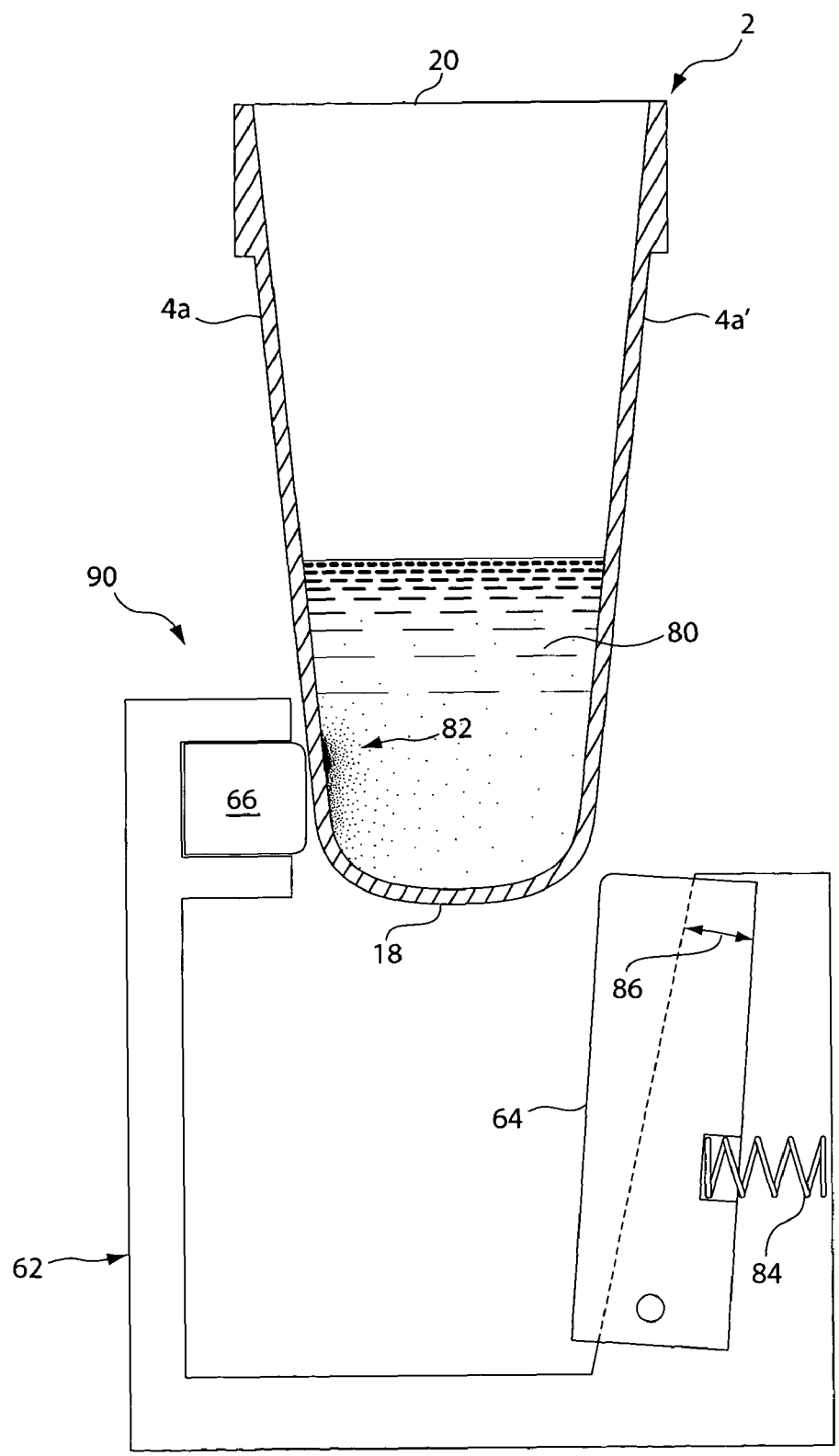
FIG. 6A is a schematic drawing of a tapered vessel entering a magnetic particle washing device and engaging with a magnet.

FIG. 6A is a schematic drawing of a tapered vessel entering a magnetic particle washing device and engaging with a magnet. The illustrative vessel 2 is used in an automated clinical diagnostic device (not shown) including a magnetic particle washing device 90 and undergoes one or more particle wash procedures. An automated clinical diagnostic device may have one or more than one magnetic particle washing device 90 station(s), for example 2, 4, 8, or 12 stations. The particle wash procedure includes the steps of diluting a reaction fluid 80, for example, a sample, in the vessel 2 with a wash solution, magnetically attracting the magnetic particles 82 in the reaction fluid 80 to the particle engagement side 4a, 4a' of the vessel 2, aspirating the reaction fluid 80 to a waste container (not shown), and washing the magnetic particles 82 with an injected wash solution (not shown).

In the magnetic particle washing device 62, according to one embodiment of the invention, the vessel 2 is kept in place in a vessel holder 62 by a lever arm 64, for example, a spring-loaded lever arm 64. As the vessel 2 is lowered into the vessel holder 62, the force of the vessel 2 compresses the spring 84 of the lever arm 64. The body of the lever arm 64 retracts into the body of the vessel holder 62 a distance 86 measured from the interior surface of the vessel holder 62 to the exterior surface of the lever arm 64. In one embodiment, the exterior surface of the vessel holder 62 is cut out to allow the lever arm 64 to pass through the vessel holder 62. The tension of the spring-loaded lever arm 64 maintains the vessel 2 in the proper orientation within the vessel holder 62.

Referring still to FIG. 6A, in one embodiment according to the invention, the vessel 2 is lowered into the vessel holder 62 and is engaged by the magnet 66. The magnet 66 first engages the vessel 2 at the narrow bottom 18 of the vessel 2. The magnetic particles 82 suspended in the fluid 80 are attracted to the magnet 66 and collect along the particle engagement side 4a, 4a' of the vessel 2 at the location where the magnet 66 is engaged with the vessel 2. The magnetic particles 82 are collected in the narrow bottom 18 portion of the vessel 2, where the magnetic particles 82 travel a short distance and low magnetic flux density is needed to pull the magnetic particles 82 out of the fluid 80. The magnet 66 then moves upward along the particle engagement side 4a, 4a' of the vessel 2 toward the top 20 of the vessel 2, carrying the magnetic particles 82 in the direction toward the top 20 of the vessel 2. In one embodiment, the magnet is a Neodymium magnet, for example, having a facing surface area in the range of about 20 mm$^2$ to about 30 mm$^2$, preferably about 25 mm$^2$, and a magnetic strength in the range of about 12,000 Gauss to about 13,000 Gauss, preferably about 12,500 Gauss [Grade 38 Neodymium magnet].

Figure 6B:
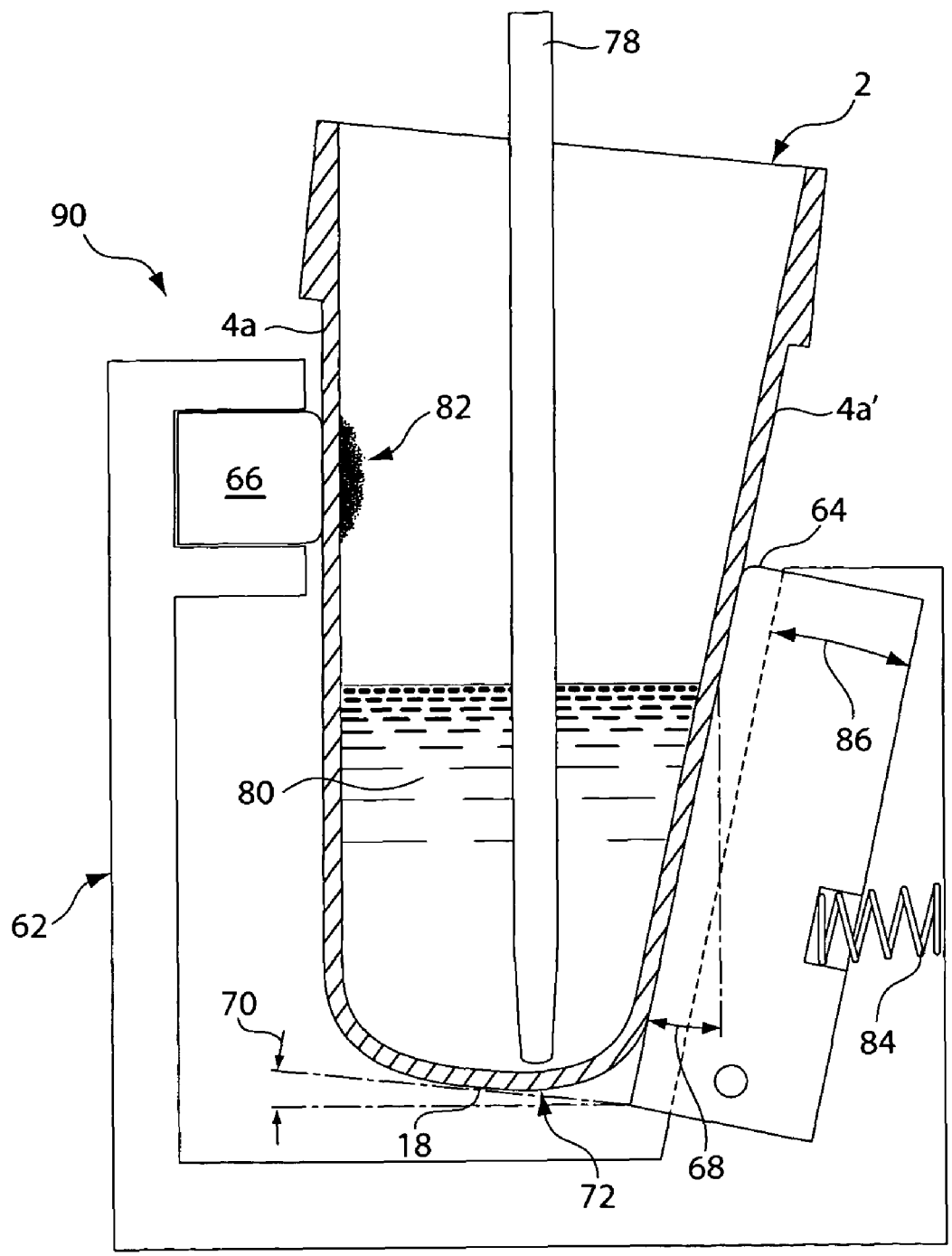
FIG. 6B is a schematic drawing of the tapered vessel in a magnetic particle washing device shown in FIG. 6A following capture of the magnetic particles to the side of the vessel, and moved out of the fluid as the magnet is moved toward the top of the vessel.

FIG. 6B is a schematic drawing of the tapered vessel in a magnetic particle washing device shown in FIG. 6A following capture of the magnetic particles on to the side of the vessel, by the magnet, and moved out of the fluid. The illustrative vessel 2 is lowered into the vessel holder 62, and the force of the spring-loaded lever arm 64 tilts the vessel 2 until the particle engagement side 4a of the vessel 2 against the magnet 66 is substantially vertical. In the tilted position, the opposite side 4a' of the vessel 2 against the lever arm 64 is held at an angle 68 of about 10 degrees to about 14 degrees relative to the vertical surface of the vessel holder 62, preferably about 12 degrees. The angle 68 of the opposite side 4a' of the vessel 2 in the tilted position is substantially equal to twice the taper angle 24 of the vessel 2 when the vessel 2 is centered about its vertical axis 28. In the same tilted position, the bottom 18 of the vessel 2 is held at an angle 70 of about 4 degrees to about 6 degrees relative to the horizontal surface of the vessel holder 62, preferably about 5 degrees. The angle 68 of the bottom 18 of the vessel 2 in the tilted position is substantially equal to the taper angle 24 of the vessel 2 when the vessel 2 is centered about its vertical axis 28.

Referring still to FIG. 6B, in one method according to the invention, as the vessel 2 is lowered into the vessel holder 62, the position of the magnet 66 moves relative to the particle engagement side 4a of the vessel 2. As the magnet 66 moves along the particle engagement side 4a of the vessel 2, the magnetic particles 82 remain attracted to the magnet 66 and move with the magnet 66 relative to the particle engagement side 4a of the vessel 2. In one embodiment, the vessel 2 is held stationary while the vessel holder 62, the magnet 66, and the magnetic particles 82 are moved in an upward direction. In another embodiment, the vessel holder 62, the magnet 66, and the magnetic particles 82 are held stationary while the vessel 2 is moved in a downward direction. By either means of moving the particles along the particles engagement side 4a, 4a', of the vessel 2, the magnetic particles 82 are moved from within the fluid 80 toward the top 20 of the vessel 2 along the particle engagement side 4a of the vessel 2 and out of the fluid 80.

With continued reference to FIG. 6B, in one method according to the invention for removing the fluid, for example, wash fluid, reagent fluid or sample fluid, the tilted vessel 2 is held in a tilted position while an aspirator probe 78 is lowered into the vessel 2 to a point of aspiration 72. The point of aspiration 72 is formed at the corner of the tilted opposite side 4a' of the vessel 2, held at an angle 68 relative to the vertical surface of the vessel holder 62, and the titled bottom 18 of the vessel 2, held at an angle 70 relative to the horizontal surface of the vessel holder 62. In this position, the fluid medium 80 within the vessel 2 flows toward the point of aspiration 72 and is aspirated out of the vessel 2 by the aspirator probe 78. The point of aspiration 72 created by the tilted vessel 2 allows a more complete aspiration than if the vessel 2 was level and aspiration was conducted across the entire surface area of the bottom 18 of the vessel 2. The tapered sides 4a, 4a', 4b, 4b' of the vessel 2 allow the vessel 2 to tilt and to assume a point of aspiration 72.

Referring still to FIG. 6B, according to one method of the invention, the magnetic particles 82 are drawn out of the fluid 80 and held above the fluid 80 along the particle engagement side 4a of the vessel 2 before the fluid 80 is aspirated out of the vessel 2. Holding the magnetic particles 82 out of the fluid 80 reduces the number of magnetic particles 82 lost during fluid aspiration.

EXAMPLE

In the following examples, a vessel containing 450 uL+/−30 uL of fluid medium and magnetic particles [Dynabeads M280, Dynal, Oslo, Denmark] was placed in a magnetic particle washing device of an automated clinical diagnostic device. If the fluid volume was below 420 uL, fluid medium was added until the desired fluid volume was reached. The magnet was moved to contact the vessel and was held stationary for about 25 seconds to separate the magnetic particles from the fluid medium. Once the magnetic particles were separated, the magnet moved upward, pulling the magnetic particles above the meniscus of the fluid medium and holding the magnetic particles above the fluid while the aspiration probe removed the fluid medium. After aspiration, the magnet was moved downward, resubmerging the magnetic particles in the fluid medium.

After the fluid was aspirated out of the vessel, rinse solution was injected into the vessel by an injector tube located above the top of the vessel. Rinse solution was injected at an angle directed toward the particle engagement side of the vessel. The magnetic particles are washed down the vessel wall thereby resuspending the magnetic particles in the wash solution. Several wash cycles may be performed, depending on the assay. In each wash cycle, the steps of magnetic separation of the particles from the fluid medium, aspiration of the fluid medium, and washing by injecting rinse solution are repeated, followed by a final aspiration of the fluid medium before analysis of the vessel contents.

Holding the magnetic particles 82 out of the fluid 80 reduces the number of magnetic particles 82 lost during aspiration to a rate of about 0.0% to about 0.5% of the total number of magnetic particles that were in the fluid medium per cycle. In trials using the same device, but retaining the magnetic particles 82 within the fluid 80 during aspiration, the number of magnetic particles 82 lost during aspiration increased to a rate of about 5% to about 20%. The percent loss was determined by measuring the absorbence of the vessel after 1 to 10 magnetic particle wash cycles at 500 nm and subtracting the measured absorbence from the average absorbence from 3 to 5 reference vessels which did not undergo magnetic particle washing.

What we claim is:

1. A device for washing magnetic particles in a vessel, comprising:
   a holder comprising,
   a) a holder lumen,
   b) a vertical surface comprising a magnet, and
   c) a lever arm,
   wherein said lever arm is mounted to a pivot point proximal to a lower end of said lever arm and is reciprocally moveable from a vertical position to a lever arm tilted position relative to the vertical surface of the holder when a vessel is received in the holder lumen between the vertical surface and said lever arm, and said lever arm is biased toward said vertical position to retain a vessel in a tilted position relative to the vertical surface of the holder.

2. The device of claim 1 wherein said lever arm comprises a spring.

3. The device of claim 1 wherein the magnet has a flat side creating a uniform magnetic flux density over the flat side for engagement with a planar particle engagement side of a vessel, wherein said planar particle engagement side of said vessel is free of any bend or arc outside the plane.

4. The device of claim 1, wherein said magnet is a Neodymium magnet and the magnetic strength is in a range of about 12,000 Gauss to about 13,000 Gauss.

5. The device of claim 1, wherein said magnet has a magnetic strength of about 12,500 Gauss.

6. The device of claim 1, wherein said magnet is movable from the bottom of the vessel towards the top of the vessel along the particle engagement side of said vessel received in the holder lumen.

* * * * *

UNITED STATES PATENT AND TRADEMARK OFFICE
CERTIFICATE OF CORRECTION

| | | |
|---|---|---|
| PATENT NO. | : 8,211,386 B2 | Page 1 of 1 |
| APPLICATION NO. | : 10/863881 | |
| DATED | : July 3, 2012 | |
| INVENTOR(S) | : Mark Talmer | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 895 days.

Signed and Sealed this
Fifth Day of November, 2013

Teresa Stanek Rea
*Deputy Director of the United States Patent and Trademark Office*